US012516332B2

(12) United States Patent
Thompson et al.

(10) Patent No.: US 12,516,332 B2
(45) Date of Patent: Jan. 6, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventors: Bradley G. Thompson, Calgary (CA); Jill L. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/194,480

(22) Filed: Apr. 30, 2025

(65) Prior Publication Data

US 2025/0257362 A1 Aug. 14, 2025

Related U.S. Application Data

(60) Continuation of application No. 18/933,567, filed on Oct. 31, 2024, which is a division of application No. 18/518,177, filed on Nov. 22, 2023, now Pat. No. 12,435,338.

(51) Int. Cl.
*C12N 15/117* (2010.01)
*C12N 15/86* (2006.01)

(52) U.S. Cl.
CPC ............ *C12N 15/117* (2013.01); *C12N 15/86* (2013.01); *C12N 2310/141* (2013.01); *C12N 2750/14143* (2013.01)

(58) Field of Classification Search
CPC ............................. C12N 15/117; C12N 15/86; C12N 2310/141; C12N 2750/14143
See application file for complete search history.

(56) References Cited

U.S. PATENT DOCUMENTS

| | | | | |
|---|---|---|---|---|
| 11,085,055 | B2 | 8/2021 | Mallol et al. | |
| 11,162,102 | B2 * | 11/2021 | Minshull .............. | C12N 9/1241 |
| 11,530,423 | B1 | 12/2022 | Thompson | |
| 11,873,505 | B2 | 1/2024 | Thompson | |
| 12,018,274 | B2 | 6/2024 | Thompson | |
| 12,134,770 | B1 | 11/2024 | Thompson | |
| 2022/0220187 | A1 | 7/2022 | Sabzevari et al. | |
| 2022/0356489 | A1 | 11/2022 | Thompson | |
| 2024/0026377 | A1 | 1/2024 | Thompson | |

FOREIGN PATENT DOCUMENTS

| | | | |
|---|---|---|---|
| CA | 2721333 | A1 | 10/2009 |

OTHER PUBLICATIONS

NCBI Reference Sequence: NM_025239.4. *Homo sapiens* programmed cell death 1 ligand 2 (PDCD1LG2), mRNA. Aug. 14, 2023. (Year: 2023).*

Lam et al. 2015. siRNA Versus miRNA as Therapeutics for Gene Silencing. Molec. Ther. Nuc. Ac. 4:e252. doi: 10.1038/mtna.2015.23. (Year: 2015).*

Ying et al. 2008. The MicroRNA (miRNA): Overview of the RNA Genes that Modulate Gene Function. Mol. Biotechnol. 38:257-268. doi: 10.1007/s12033-007-9013-8 (Year: 2008).*

Gorski, S., Vogel, J. & Doudna, J. RNA-based recognition and targeting: sowing the seeds of specificity. Nat Rev Mol Cell Biol 18, 215-228 (2017). (Year: 2017).*

Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).*

Van den Berg, et al., pp. 1-12, Molecular Therapy—Nucleic Acids, vol. 5, 2016 (Year: 2016).*

Wang et al. "Adeno-associated virus vector as a platform for gene therapy delivery." Nature reviews Drug discovery 18.5 (2019): 358-378.

Barnum, Kevin J., and Matthew J. O'Connell. "Cell cycle regulation by checkpoints." Cell cycle control: mechanisms and protocols (2014): 29-40.

O'Brien et al. "Overview of microRNA biogenesis, mechanisms of actions, and circulation." Frontiers in endocrinology 9 (2018): 402.

Zhang et al. "The risks of miRNA therapeutics: in a drug target perspective." Drug design, development and therapy (2021): 721-733.

Zhang et al. "Functions of immune checkpoint molecules beyond immune evasion." Regulation of cancer immune checkpoints: molecular and cellular mechanisms and therapy (2020): 201-226.

Kozomara et al. "miRBase: from microRNA sequences to function." Nucleic acids research 47.D1 (2019): D155-D162.

Jüppner, H. "Functional properties of the PTH/PTHrP receptor." Bone 17.2 (1995): S39-S42.

Ha et al. "Interspecies regulation of microRNAs and their targets." Biochimica et Biophysica Acta (BBA)-Gene Regulatory Mechanisms 1779.11 (2008): 735-742.

Bottoni et al. "Targeting BTK through microRNA in chronic lymphocytic leukemia." Blood, The Journal of the American Society of Hematology 128.26 (2016): 3101-3112.

Brutons Tyrosine Kinase Genbank Sequence (2023).

(Continued)

*Primary Examiner* — Neil P Hammell
*Assistant Examiner* — Amanda M Zahorik
(74) *Attorney, Agent, or Firm* — Gowling WLG (Canada) LLP

(57) ABSTRACT

Embodiments of the present disclosure relate to a composition that comprises a recombinant plasmid (RP) with a sequence of nucleic acids. The sequence comprise a start region, an end region and an insert positioned between the start region and the end region. The insert encodes for a sequence of micro interfering ribonucleic acid (miRNA) that may be complimentary to a sequence of target messenger RNA (mRNA) that encodes for translation of a target biomolecule. The miRNA can cause the target mRNA to be degraded or inactivated, thereby causing a decrease in bioavailability of the target biomolecule because it is degraded or inactivated by the miRNA, thereby decreasing the bioavailability of the target biomolecule. In some embodiments of the present disclosure, the target biomolecule is an immune checkpoint protein.

2 Claims, No Drawings

Specification includes a Sequence Listing.

(56) References Cited

OTHER PUBLICATIONS

Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Yuasa et al. Low efficiency ID02 enzymes are conserved in lower vertebrates, whereas higher efficiency IDO1 enzymes are dispensable. FEBS Journal 282 (2015) 2735-2745. (Year: 2015).
Nature (2010. Gene Expression. Scitable. Available online at Nature.com) <https://www.nature.com/scitable/topicpage/gene-expression-14121669> (2010).
GenBank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
Genbank FLT3 Sequence (2024).
NCBI Nucleotide Sequence for PARP, search performed Dec. 26, 2024 (2024).
Tritschler et al. "Concepts and limitations for learning developmental trajectories from single cell genomics." Development 146.12 (2019): dev170506.
Kondratov et al. "Direct head-to-head evaluation of recombinant adeno-associated viral vectors manufactured in human versus insect cells." Molecular Therapy 25.12 (2017): 2661-2675.
Ahmad et al .Adaptive selection in the evolution of programmed cell death-1 and its ligands in vertebrates. Aging (Albany NY). Feb. 11, 2020;12(4):3516-3557. (Year: 2020).
NCBI Reference Sequence: NC_000009.12. *Homo sapiens* chromosome 9, GRCh38.p14 Primary Assembly. (gene="CD274", gene_synonym=B7-H; B7H1; hPD-L1; PD-L1; PDCD1L1; PDCD1LG1; PDL1). Oct. 7, 2023. (Year: 2023).
Qiniou et al. Extraordinary diversity of the CD28/CTLA4 family across jawed vertebrates. Front. Immunol., Nov. 12, 2024. Sec. Comparative Immunology. vol. 15—2024. (Year: 2024).
NCBI Reference Sequence: NG_011502.1. *Homo sapiens* cytotoxic T-lymphocyte-associated protein 4 (CTLA4) on chromosome 2. Mar. 11, 2009. (Year: 2009).
NCBI Reference Sequence: NR_030784.1. *Homo sapiens* microRNA 155 (MIR155), microRNA. Nov. 24, 2009. (Year: 2009).
Vaddi et al. CTLA4 mRNA is downregulatA4 mRNA is downregulated by miR-155 in regulatory T cells, and reduced blood CTLA4 levels are associated with poor prognosis in metastatic melanoma patients. Front. Immunol. Apr. 30, 2023.Sec. Cancer Immunity and Immunotherapy. vol. 14—2023. (Year: 2023).
GenBank: LM608503.1. TPA: *Homo sapiens* microRNA hsa-mir-153-1 precursor. Mar. 3, 2015. (Year: 2015).
NCBI Reference Sequence: NG_028155.1. *Homo sapiens* indoleamine 2,3-dioxygenase 1 (IDO1), RefSeqGene on chromosome 8. May 18, 2020. (Year: 2020).

* cited by examiner

COMPOSITION FOR REGULATING PRODUCTION OF INTERFERING RIBONUCLEIC ACID

CROSS-REFERENCE TO RELATED APPLICATION

The present application is a continuation of U.S. patent application Ser. No. 18/933,567 filed Oct. 31, 2024, entitled "Composition For Regulating Production Of Interfering Ribonucleic Acid", which is a divisional application of U.S. patent application Ser. No. 18/518,177 filed Nov. 22, 2023, entitled "Composition For Regulating Production Of Interfering Ribonucleic Acid" currently pending, the entirety of these are incorporated herein by reference.

SEQUENCE LISTING

This application contains a Sequence Listing electronically submitted via Patent Center to the United States Patent and Trademark Office as an XML Document file entitled "A8149361US-Sequence Listing.xml" created on 2023 Nov. 17 and having a size of 49,999 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA, that will suppress checkpoint molecule overexpression or mis-expression.

BACKGROUND

Bioactive molecules, including checkpoint molecules, are necessary for the homeostatic control of biological systems. When bioactive molecules are over-expressed or mis-expressed, homeostasis is lost, and disease is often the result. As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro interfering ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is an immune checkpoint molecule. In some embodiments of the present disclosure, the target biomolecule is an immune checkpoint molecule such as PD-1. In some embodiments of the present disclosure, the target biomolecule is an immune checkpoint molecule such as PD-L1. In some embodiments of the present disclosure, the target biomolecule is an immune checkpoint molecule such as PD-L2. In some embodiments of the present disclosure, the target biomolecule is an immune checkpoint molecule such as CTLA4. In some embodiments of the present disclosure, the target biomolecule is an immune checkpoint molecule such as IDO1. In some embodiments of the present disclosure, the target biomolecule participates, directly or indirectly, in one or more immune responses. For example, the target biomolecule may be an immune checkpoint molecule that is a protein, a protein-protein complex—such as a receptor ligand pair—or other type of biomolecule that directly or indirectly inhibits an immune response or that directly or indirectly stimulates an immune response.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of PD-1.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets mRNA of PD-L1.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets mRNA of PD-L2.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets mRNA of CTLA4.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets mRNA of IDO1.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, or SEQ ID NO. 6, to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example PD-1. A first approach utilizes gene vectors containing nucleotide sequences for increasing the endogenous production of one or more sequences of miRNA, which are complete or partial sequences and/or combinations thereof, that target and silence the mRNA of PD-1, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PD-L1. A first approach utilizes gene vectors containing nucleotide sequences for increasing the endogenous production of one or more sequences of miRNA, which are complete or partial sequences and/or combinations thereof, that target and silence the mRNA of PD-L1, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PD-L2. A first approach utilizes gene vectors containing nucleotide sequences for increasing the endogenous production of one or more sequences of miRNA, which are complete or partial sequences and/or combinations thereof, that target and silence the mRNA of PD-L2, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example CTLA4. A first approach utilizes gene vectors containing nucleotide sequences for increasing the endogenous production of one or more sequences of miRNA, which are complete or partial sequences and/or combinations thereof, that target and silence the mRNA of CTLA4, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example IDO1. A first approach utilizes gene vectors containing nucleotide sequences for increasing the endogenous production of one or more sequences of miRNA, which are complete or partial sequences and/or combinations thereof, that target and silence the mRNA of IDO1, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a checkpoint molecule that is found within a subject. A biomolecule may be endogenous or exogenous to a subject and when bioavailable the biomolecule may inhibit or stimulate an immune process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is PD-1.

In some embodiments of the present disclosure, the target biomolecule is PD-L1.

In some embodiments of the present disclosure, the target biomolecule is PD-L2.

In some embodiments of the present disclosure, the target biomolecule is CTLA4.

In some embodiments of the present disclosure, the target biomolecule is IDO1.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as PD-1, PD-L1, PD-L2, CTLA4, or IDO1. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as PD-1, PD-L1, PD-L2, CTLA4, or IDO1.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the viral vector is a double stranded DNA virus, a single stranded DNA virus, a single stranded RNA virus, or a double stranded RNA virus. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient's body mass. In some embodiments of the present disclosure, the therapeutically effective amount of the composition that is administered to the patient is about $1\times10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1\times10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with examples being PD-1, PD-L1, PD-L2, CTLA4, or IDO1. The RP is comprised of AAV2 inverted terminal repeats (ITRs), a composite CASI promoter, a human growth hormone (HGH) signal peptide followed by a miRNA expression cassette containing up to six different miRNAs targeting PD-1, PD-L1, PD-L2, CTLA4, or IDO1, followed by a Woodchuck Hepatitis Virus post-transcriptional regulatory clement (WPRE) and an SV40 polyA signal.

```
SEQ ID NO. 1 (backbone sequencc No. 1):
5'

aatcaacctctggattacaaaatttgtgaaagattgactggtattcttaactatgttgctccttttacgctatgtggatacgctgctttaatgcctttgt

atcatgctattgcttcccgtatggctttcattttctcctccttgtataaatcctggttgctgtctctttatgaggagttgtggcccgttgtcaggcaac

gtggcgtggtgtgcactgtgtttgctgacgcaacccccactggttggggcattgccaccacctgtcagctcctttccgggactttcgctttccc

cctccctattgccacggcggaactcatcgccgcctgccttgcccgctgctggacaggggctcggctgttgggcactgacaattccgtggtgt

tgtcggggaaatcatcgtcctttccttggctgctcgcctgtgttgccacctggattctgcgcgggacgtccttctgctacgtcccttcggccctc

aatccagcggaccttccttcccgcggcctgctgccggctctgcggcctcttccgcgtcttcgccttcgccctcagacgagtcggatctcccttt

gggccgcctccccgcctaagcttatcgataccgtcgagatctaacttgtttattgcagcttataatggttacaaataaagcaatagcatcacaaa

tttcacaaataaagcatttttttcactgcattctagttgtggtttgtccaaactcatcaatgtatcttatcatgtctggatctcgacctcgactagagc

atggctacgtagataagtagcatggcgggttaatcattaactacaaggaacccctagtgatggagttggccactccctctctgcgcgctcgct

cgctcactgaggccgggcgaccaaaggtcgcccgacgcccgggctttgcccgggcggcctcagtgagcgagcgagcgcgcagctgg

cgtaatagcgaagaggcccgcaccgatcgcccttcccaacagttgcgcagcctgaatggcgaatggcgattccgttgcaatggctggcgg

taatattgttctggatattaccagcaaggccgatagtttgagttcttctactcaggcaagtgatgttattactaatcaaagaagtattgcgacaac

ggttaatttgcgtgatggacagactcttttactcggtggcctcactgattataaaaacacttctcaggattctggcgtaccgttcctgtctaaaatc

cctttaatcggcctcctgtttagctcccgctctgattctaacgaggaaagcacgttatacgtgctcgtcaaagcaaccatagtacgcgccctgt

agcggcgcattaagcgcggcgggtgtggtggttacgcgcagcgtgaccgctacacttgccagcgccctagcgcccgctcctttcgctttctt

cccttcctttctcgccacgttcgccggctttccccgtcaagctctaaatcgggggctccctttagggttccgatttagtgctttacggcacctcga

ccccaaaaaacttgattagggtgatggttcacgtagtgggccatcgccctgatagacggtttttcgccctttgacgttggagtccacgttcttta

atagtggactcttgttccaaactggaacaacactcaaccctatctcggtctattcttttgatttataagggattttgccgatttcggcctattggttaa

aaaatgagctgatttaacaaaaatttaacgcgaattttaacaaaatattaacgtttacaatttaaatatttgcttatacaatcttcctgtttttggggct

tttctgattatcaaccggggtacatatgattgacatgctagttttacgattaccgttcatcgattctcttgtttgctccagactctcaggcaat gacct

gatagcctttgtagagacctctcaaaaatagctaccctctccggcatgaatttatcagctagaacggttgaatatcatattgatggtgatttgact

gtctccggcctttctcacccgtttgaatctttacctacacattactcaggcattgcatttaaaatatatgagggttctaaaaatttttatccttgcgttg

aaataaaggcttctcccgcaaaagtattacagggtcataatgtttttggtacaaccgatttagctttatgctctgaggctttattgcttaattttgcta

attctttgccttgcctgtatgatttattggatgttggaattcctgatgcggtattttctccttacgcatctgtgcggtatttcacaccgcatatggtgca

ctctcagtacaatctgctctgatgccgcatagttaagccagccccgacacccgccaacacccgctgacgcgccctgacgggcttgtctgctc
```

-continued ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccggggcgccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg -continued gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgcc

3'

SEQ ID NO. 2 (miRNA expression cassette No. 2-PD-1):
5' gctagcatcgataccgtcgctatgtgctggaggcttgctgaaggctgtatgctgtacctaagaactgcatcctggccgttttggcctctgactg acggccaggatggttcttaggtacaggacacaaggcctgttactagcactcacatggaacaaatggcctctagcctggaggcttgctgaag gctgtatgctgtcgtaaagccaataggttagtcccgttttggcctctgactgacgggactaaccttggctttacgacaggacacaaggcctgtt actagcactcacatggaacaaatggcctctagcctggaggcttgctgaaggctgtatgctgagagagaccgcaaattaccggacggttttg gcctctgactgaccgtgcctgtaatgcggtctctctcaggacacaaggcctgttactagcactcacatggaacaaatggcctctctagaat

3'

SEQ ID NO. 3 (miRNA expression cassette No. 3-PD-L1):
5' gctagcatcgataccgtcgctatgtgctggaggcttgctgaaggctgtatgctgagagacttacttgtagatgctgcgttttggcctctgactga cgcagcatctaagtaagtctctcaggacacaaggcctgttactagcactcacatggaacaaatggcctctagcctggaggcttgctgaaggc tgtatgctgactatttcatcatactctcacccgttttggcctctgactgacgggtgagagtgatgaaatagtcaggacacaaggcctgttactag cactcacatggaacaaatggcctctagcctggaggcttgctgaaggctgtatgctgatatgaatgacaatcacagccgagttttggcctctga ctgacgtggctgtgagtcattcatatcaggacacaaggcctgttactagcactcacatggaacaaatggcctctctagaat

3'

SEQ ID NO. 4 (miRNA expression cassette No. 4-PD-L2):
5'
gctagcatcgataccgtcgctatgtgctggaggcttgctgaaggctgtatgctgacaatcaacattggcagtagctcgttttggcctctgactg acgagctactgcatgttgattgtcaggacacaaggcctgttactagcactcacatggaacaaatggcctctagcctggaggcttgctgaagg ctgtatgctgaataagcctttatccatagtcccgttttggcctctgactgacgggactatggaaaggcttattcaggacacaaggcctgttacta gcactcacatggaacaaatggcctctagcctggaggcttgctgaaggctgtatgctgacaactgtctcaaattactgctcgttttggcctctga ctgacgagcagtaatgagacagttgtcaggacacaaggcctgttactagcactcacatggaacaaatggcctctctagaat

3'

SEQ ID NO. 5 (miRNA expression cassette No. 5-CTLA4):
5' gctagcatcgataccgtcgctatgtgctggaggcttgctgaaggctgtatgctgtcactcacctttgtgcagaagacgttttggcctctgactg acgtcttctgcaaaggtgagtgacaggacacaaggcctgttactagcactcacatggaacaaatggcctctagcctggaggcttgctgaag gctgtatgctggttcttagcctatctcaagtagcgttttggcctctgactgacgctacttgagaggctaagacacaggacacaaggcctgttac tagcactcacatggaacaaatggcctctagcctggaggcttgctgaaggctgtatgctggtctatgtctaaattccagcagcgttttggcctct gactgacgctgctggaatagacatgacacaggacacaaggcctgttactagcactcacatggaacaaatggcctctctagaat

3'

SEQ ID NO. 6 (miRNA expression cassette No. 6-IDO1):
5' gctagcatcgataccgtcgctatgtgctggaggcttgctgaaggctgtatgctgctcacttgaattgcttaccgctccgttttggcctctgactg acggagcggtaagattcaagtgagcaggacacaaggcctgttactagcactcacatggaacaaatggcctctagcctggaggcttgctga aggctgtatgctgtgtctgatcctatctcaagtagcgttttggcctctgactgacgctacttgagaggctaagacacaggacacaaggcctgtt actagcactcacatggaacaaatggcctctagcctggaggcttgctgaaggctgtatgctgatgtttccgggaaacagtgactcgttttggcc tctgactgacgattcactgtcccggaaacatcaggacacaaggcctgttactagcactcacatggaacaaatggcctctctagaat

3'

-continued

SEQ ID NO: 7 = SEQ ID NO: 1 + SEQ ID NO: 2
5'
aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctccctttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatottatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac -continued tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcggggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaaggggcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtacctaagaactgcatcctggccgttttggcctctgactgacggccaggatggttctt aggtacaggacacaaggcctgttactagcactcacatggaacaaatggcctctagcctggaggcttgctgaaggctgtatgctgtcgtaaag ccaataggttagtcccgttttggcctctgactgacgggactaaccttggctttacgacaggacacaaggcctgttactagcactcacatggaa caaatggcctctagcctggaggcttgctgaaggctgtatgctgagagagaccgcaaattaccggacggttttggcctctgactgaccgtcct gtaatgcggtctctctcaggacacaaggcctgttactagcactcacatggaacaaatggcctctctagaat

3'

SEQ ID NO: 8 = SEQ ID NO: 1 + SEQ ID NO: 3
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg -continued cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct -continued aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgagagacttacttgtagatgctgcgttttggcctctgactgacgcagcatctaagtaagt ctctcaggacacaaggcctgttactagcactcacatggaacaaatggcctctagcctggaggcttgctgaaggctgtatgctgactatttcatc atactctcacccgttttggcctctgactgacgggtgagagtgatgaaatagtcaggacacaaggcctgttactagcactcacatggaacaaat ggcctctagcctggaggcttgctgaaggctgtatgctgatatgaatgacaatcacagccgagttttggcctctgactgacgtggctgtgagtc attcatatcaggacacaaggcctgttactagcactcacatggaacaaatggcctctctagaat

3'

SEQ ID NO: 9 = SEQ ID NO: 1 + SEQ ID NO: 4
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct -continued gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggacc ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg -continued gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgacaatcaacattggcagtagctcgttttggcctctgactgacgagctactgcatgttg attgtcaggacacaaggcctgttactagcactcacatggaacaaatggcctctagcctggaggcttgctgaaggctgtatgctgaataagcct ttatccatagtcccgttttggcctctgactgacgggactatggaaaggcttattcaggacacaaggcctgttactagcactcacatggaacaaa tggcctctagcctggaggcttgctgaaggctgtatgctgacaactgtctcaaattactgctcgttttggcctctgactgacgagcagtaatgag acagttgtcaggacacaaggcctgttactagcactcacatggaacaaatggcctctctagaat

3'

SEQ ID NO: 10 = SEQ ID NO: 1 + SEQ ID NO: 5
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcggggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctgggtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt -continued ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatgggggcgggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtcactcacctttgtgcagaagacgttttggcctctgactgacgtcttctgcaaaggtga gtgacaggacacaaggcctgttactagcactcacatggaacaaatggcctctagcctggaggcttgctgaaggctgtatgctggttcttagc ctatctcaagtagcgttttggcctctgactgacgctacttgagaggctaagacacaggacacaaggcctgttactagcactcacatggaacaa -continued atggcctctagcctggaggcttgctgaaggctgtatgctggtctatgtctaaattccagcagcgttttggcctctgactgacgctgctggaata gacatgacacaggacacaaggcctgttactagcactcacatggaacaaatggcctctctagaat

3'

SEQ ID NO: 11 = SEQ ID NO: 1 + SEQ ID NO: 6
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggggggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaa cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactgggaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc -continued agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccacccccaattttgtatttatttattttttaattattttgtgcagcgatggggggggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgcccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgctcacttgaattgcttaccgctccgttttggcctctgactgacggagcggtaagattca agtgagcaggacacaaggcctgttactagcactcacatggaacaaatggcctctagcctggaggcttgctgaaggctgtatgctgtgtctga tcctatctcaagtagcgttttggcctctgactgacgctacttgagaggctaagacacaggacacaaggcctgttactagcactcacatggaac aaatggcctctagcctggaggcttgctgaaggctgtatgctgatgtttccgggaaacagtgactcgttttggcctctgactgacgattcactgt cccggaaacatcaggacacaaggcctgttactagcactcacatggaacaaatggcctctctagaat

3'

As will be appreciated by those skilled in the art. because the recombinant plasmid is a circular vector, the one or more sequences of the miRNA expression cassettes may be connected at the 3' end of SEQ ID NO. 1, as shown in SEQ ID NO. 7-11 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1-Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) that comprises a sequence of nucleotides that is 100% identical to the full length of SEQ ID NO. 9.

2. The composition of claim 1, wherein the RP is encased in a protein coat, a lipid vesicle, or any combination thereof.

* * * * *

SEQUENCE LISTING

```
Sequence total quantity: 11
SEQ ID NO: 1            moltype = DNA  length = 5883
FEATURE                 Location/Qualifiers
source                  1..5883
                        mol_type = other DNA
                        organism = synthetic construct
SEQUENCE: 1
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
```

```
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gcc                                                               5883
```

```
SEQ ID NO: 2            moltype = DNA  length = 460
FEATURE                 Location/Qualifiers
source                  1..460
                        mol_type = other DNA
                        organism = synthetic construct
SEQUENCE: 2
gctagcatcg ataccgtcgc tatgtgctgg aggcttgctg aaggctgtat gctgtaccta  60
agaactgcat cctggccgtt ttggcctctg actgacggcc aggatggttc ttaggtacag  120
gacacaaggc ctgttactag cactcacatg gaacaaatgg cctctagcct ggaggcttgc  180
tgaaggctgt atgctgtcgt aaagccaata ggttagtccc gttttggcct ctgactgacg  240
ggactaacct tggctttacg acaggacaca aggcctgtta ctagcactca catggaacaa  300
atggcctcta gcctggaggc ttgctgaagg ctgtatgctg agagagaccg caaattaccg  360
gacggttttg gcctctgact gaccgtcctg taatgcggtc tctctcagga cacaaggcct  420
gttactagca ctcacatgga acaaatggcc tctctagaat                        460
```

```
SEQ ID NO: 3            moltype = DNA  length = 456
FEATURE                 Location/Qualifiers
source                  1..456
                        mol_type = other DNA
                        organism = synthetic construct
SEQUENCE: 3
gctagcatcg ataccgtcgc tatgtgctgg aggcttgctg aaggctgtat gctgagagac  60
ttacttgtag atgctgcgtt ttggcctctg actgacgcag catctaagta agtctctcag  120
gacacaaggc ctgttactag cactcacatg gaacaaatgg cctctagcct ggaggcttgc  180
tgaaggctgt atgctgacta tttcatcata ctctcacccg ttttggcctc tgactgacgg  240
gtgagagtga tgaaatagtc aggacacaag gcctgttact agcactcaca tggaacaaat  300
ggcctctagc ctggaggctt gctgaaggct gtatgctgat atgaatgaca atcacagccg  360
agttttggcc tctgactgac gtggctgtga gtcattcata tcaggacaca aggcctgtta  420
ctagcactca catggaacaa atggcctctc tagaat                            456
```

```
SEQ ID NO: 4            moltype = DNA  length = 456
FEATURE                 Location/Qualifiers
source                  1..456
```

```
                         mol_type = other DNA
                         organism = synthetic construct
SEQUENCE: 4
gctagcatcg ataccgtcgc tatgtgctgg aggcttgctg aaggctgtat gctgacaatc  60
aacattggca gtagctcgtt ttggcctctg actgacgagc tactgcatgt tgattgtcag  120
gacacaaggc ctgttactag cactcacatg gaacaaatgg cctctagcct ggaggcttgc  180
tgaaggctgt atgctgaata agcctttatc catagtcccg ttttggcctc tgactgacgg  240
gactatggaa aggcttattc aggacacaag gcctgttact agcactcaca tggaacaaat  300
ggcctctagc ctggaggctt gctgaaggct gtatgctgac aactgtctca aattactgct  360
cgttttggcc tctgactgac gagcagtaat gagacagttg tcaggacaca aggcctgtta  420
ctagcactca catggaacaa atggcctctc tagaat                           456

SEQ ID NO: 5             moltype = DNA  length = 456
FEATURE                  Location/Qualifiers
source                   1..456
                         mol_type = other DNA
                         organism = synthetic construct
SEQUENCE: 5
gctagcatcg ataccgtcgc tatgtgctgg aggcttgctg aaggctgtat gctgtcactc  60
acctttgtgc agaagacgtt ttggcctctg actgacgtct tctgcaaagg tgagtgacag  120
gacacaaggc ctgttactag cactcacatg gaacaaatgg cctctagcct ggaggcttgc  180
tgaaggctgt atgctggttc ttagcctatc tcaagtagcg ttttggcctc tgactgacgc  240
tacttgagag gctaagacac aggacacaag gcctgttact agcactcaca tggaacaaat  300
ggcctctagc ctggaggctt gctgaaggct gtatgctggt ctatgtctaa attccagcag  360
cgttttggcc tctgactgac gctgctggaa tagacatgac acaggacaca aggcctgtta  420
ctagcactca catggaacaa atggcctctc tagaat                           456

SEQ ID NO: 6             moltype = DNA  length = 458
FEATURE                  Location/Qualifiers
source                   1..458
                         mol_type = other DNA
                         organism = synthetic construct
SEQUENCE: 6
gctagcatcg ataccgtcgc tatgtgctgg aggcttgctg aaggctgtat gctgctcact  60
tgaattgctt accgctccgt tttggcctct gactgacgga gcggtaagat tcaagtgagc  120
aggacacaag gcctgttact agcactcaca tggaacaaat ggcctctagc ctggaggctt  180
gctgaaggct gtatgctgtg tctgatccta tctcaagtag cgttttggcc tctgactgac  240
gctacttgag aggctaagac acaggacaca aggcctgtta ctagcactca catggaacaa  300
atggcctcta gcctggaggc ttgctgaagg ctgtatgctg atgtttccgg gaaacagtga  360
ctcgttttgg cctctgactg acgattcact gtcccggaaa catcaggaca caaggcctgt  420
tactagcact cacatggaac aaatggcctc tctagaat                         458

SEQ ID NO: 7             moltype = DNA  length = 6343
FEATURE                  Location/Qualifiers
source                   1..6343
                         mol_type = other DNA
                         organism = synthetic construct
SEQUENCE: 7
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
```

-continued

```
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tccccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgtac  5940
ctaagaactg catcctggcc gttttggcct ctgactgacg gccaggatgg ttcttaggta  6000
caggacacaa ggcctgttac tagcactcac atggaacaaa tggcctctag cctggaggct  6060
tgctgaaggc tgtatgctgt cgtaaagcca ataggttagt cccgttttgg cctctgactg  6120
acgggactaa ccttggcttt acgacaggac acaaggcctg ttactagcac tcacatggaa  6180
caaatggcct ctagcctgga ggcttgctga aggctgtatg ctgagagaga ccgcaaatta  6240
ccggacggtt ttggcctctg actgaccgtc ctgtaatgcg gtctctctca ggacacaagg  6300
cctgttacta gcactcacat ggaacaaatg gcctctctag aat                    6343

SEQ ID NO: 8            moltype = DNA  length = 6339
FEATURE                 Location/Qualifiers
source                  1..6339
```

mol_type = other DNA
organism = synthetic construct
SEQUENCE: 8
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc taagcttatc 600
gataccgtcg agatctaact tgtttattgc agcttataat ggttacaaat aaagcaatag 660
catcacaaat ttcacaaata aagcattttt ttcactgcat tctagttgtg gtttgtccaa 720
actcatcaat gtatcttatc atgtctggat ctcgacctcg actagagcat ggctacgtag 780
ataagtagca tggcgggtta atcattaact acaaggaacc cctagtgatg gagttggcca 840
ctccctctct gcgcgctcgc tcgctcactg aggccgggcg accaaaggtc gcccgacgcc 900
cgggctttgc ccgggcggcc tcagtgagcg agcgagcgcg cagctggcgt aatagcgaag 960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgcc ctagcgcccg ctcctttcgc tttcttccct tcctttctcg ccacgttcgc 1440
cggctttccc cgtcaagctc taaatcgggg gctcccttta gggttccgat ttagtgcttt 1500
acggcacctc gaccccaaaa aacttgatta gggtgatggt tcacgtagtg ggccatcgcc 1560
ctgatagacg gtttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgtttttgg tacaaccgat 2160
ttagctttat gctctgaggc tttattgctt aattttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctatttttat aggttaatgt 2520
catgataata atggtttctt agacgtcagg tggcactttt cggggaaatg tgcgcggaac 2580
ccctatttgt ttatttttct aaatacattc aaatatgtat ccgctcatga gacaataacc 2640
ctgataaatg cttcaataat attgaaaaag gaagagtatg agtattcaac atttccgtgt 2700
cgcccttatt cccttttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
ttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagataccta cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggccttttt 4320
acggttcctg gccttttgct ggccttttgc tcacatgttc tttcctgcgt tatcccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctccccgcg cgttggccga ttcattaatg cagcagctgc gcgctcgctc gctcactgag 4560

```
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgaga  5940
gacttacttg tagatgctgc gttttggcct ctgactgacg cagcatctaa gtaagtctct  6000
caggacacaa ggcctgttac tagcactcac atggaacaaa tggcctctag cctggaggct  6060
tgctgaaggc tgtatgctga ctatttcatc atactctcac ccgttttggc ctctgactga  6120
cgggtgagag tgatgaaata gtcaggacac aaggcctgtt actagcactc acatggaaca  6180
aatggcctct agcctggagg cttgctgaag gctgtatgct gatatgaatg acaatcacag  6240
ccgagttttg gcctctgact gacgtggctg tgagtcattc atatcaggac acaaggcctg  6300
ttactagcac tcacatggaa caaatggcct ctctagaat                        6339

SEQ ID NO: 9            moltype = DNA  length = 6339
FEATURE                 Location/Qualifiers
source                  1..6339
                        mol_type = other DNA
                        organism = synthetic construct
SEQUENCE: 9
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aatttttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
```

```
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg ggggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgaca  5940
atcaacattg gcagtagctc gttttggcct ctgactgacg agctactgca tgttgattgt  6000
caggacacaa ggcctgttac tagcactcac atggaacaaa tggcctctag cctggaggct  6060
tgctgaaggc tgtatgctga ataagccttt atccatagtc ccgttttggc ctctgactga  6120
cgggactatg gaaaggctta ttcaggacac aaggcctgtt actagcactc acatggaaca  6180
aatggcctct agcctggagg cttgctgaag gctgtatgct gacaactgtc tcaaattact  6240
gctcgttttg gcctctgact gacgagcagt aatgagacag ttgtcaggac acaaggcctg  6300
ttactagcac tcacatggaa caaatggcct ctctagaat                         6339
```

```
SEQ ID NO: 10          moltype = DNA  length = 6339
FEATURE                Location/Qualifiers
source                 1..6339
                       mol_type = other DNA
                       organism = synthetic construct
SEQUENCE: 10
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg ggaaatcat cgtcctttcc ttggctgctc  420
gcctgtgttg ccacctggat tctgcgcggg acgtccttct gctacgtccc ttcggccctc  480
```

-continued

```
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tccccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
```

```
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgtca  5940
ctcacctttg tgcagaagac gttttggcct ctgactgacg tcttctgcaa aggtgagtga  6000
caggacacaa ggcctgttac tagcactcac atggaacaaa tggcctctag cctggaggct  6060
tgctgaaggc tgtatgctgg ttcttagcct atctcaagta gcgttttggc ctctgactga  6120
cgctacttga gaggctaaga cacaggacac aaggcctgtt actagcactc acatggaaca  6180
aatggcctct agcctggagg cttgctgaag gctgtatgct ggtctatgtc taaattccag  6240
cagcgttttg gcctctgact gacgctgctg gaatagacat gacacaggac acaaggcctg  6300
ttactagcac tcacatggaa caaatggcct ctctagaat                        6339

SEQ ID NO: 11           moltype = DNA  length = 6341
FEATURE                 Location/Qualifiers
source                  1..6341
                        mol_type = other DNA
                        organism = synthetic construct
SEQUENCE: 11
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
tttttgcac aacatggggg atcatgtaac tcgccttgat cgttgggaac cggagctgaa  3180
```

-continued

```
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atgggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgctc  5940
acttgaattg cttaccgctc cgttttggcc tctgactgac ggagcggtaa gattcaagtg  6000
agcaggacac aaggcctgtt actagcactc acatggaaca aatggcctct agcctggagg  6060
cttgctgaag gctgtatgct gtgtctgatc ctatctcaag tagcgttttg gcctctgact  6120
gacgctactt gagaggctaa gacacaggac acaaggcctg ttactagcac tcacatggaa  6180
caaatggcct ctagcctgga ggcttgctga aggctgtatg ctgatgtttc cgggaaacag  6240
tgactcgttt tggcctctga ctgacgattc actgtcccgg aaacatcagg acacaaggcc  6300
tgttactagc actcacatgg aacaaatggc ctctctagaa t                      6341
```